US006966317B2

(12) United States Patent
Bardel et al.

(10) Patent No.: US 6,966,317 B2
(45) Date of Patent: Nov. 22, 2005

(54) INDIVIDUAL RESPIRATORY GAS SUPPLY DEVICE INCLUDING A RESPIRATORY MASK AND A FACIAL RESPIRATOR

(75) Inventors: Michel Bardel, Maurepas (FR); Nicolas Bloch, Fontenay-Aux-Rose (FR); Patrice Martinez, Le Perray (FR)

(73) Assignee: Intertechnique, Plaiser (FR)

( * ) Notice: Subject to any disclaimer, the term of this patent is extended or adjusted under 35 U.S.C. 154(b) by 288 days.

(21) Appl. No.: 10/614,937

(22) Filed: Jul. 8, 2003

(65) Prior Publication Data

US 2004/0099265 A1 May 27, 2004

(51) Int. Cl.[7] ........................ A62B 18/02; A61M 16/00
(52) U.S. Cl. ........................... 128/205.25; 128/204.26; 128/206.28; 128/207.18
(58) Field of Search ...................... 128/204.26, 205.25, 128/206.27, 206.28, 207.11, 207.18

(56) References Cited

U.S. PATENT DOCUMENTS 2,185,997 A * 1/1940 Heidbrink .............. 128/204.29
2,383,649 A * 8/1945 Heidbrink .............. 128/205.25
4,378,011 A * 3/1983 Warncke et al. ....... 128/204.26
4,392,490 A * 7/1983 Mattingly et al. ..... 128/202.27
RE31,424 E * 10/1983 Ernsting et al. ....... 128/201.18
4,986,269 A * 1/1991 Hakkinen .............. 128/204.23
5,348,000 A * 9/1994 Teves .................... 128/204.18
5,630,412 A 5/1997 Dubruille et al.
5,649,532 A * 7/1997 Griffiths ................ 128/206.24
5,662,101 A * 9/1997 Ogden et al. .......... 128/205.25
6,012,455 A * 1/2000 Goldstein .............. 128/207.18

FOREIGN PATENT DOCUMENTS

EP A 0691871 5/1997

* cited by examiner

*Primary Examiner*—Henry Bennett
*Assistant Examiner*—Dinnatia Doster-Greene
(74) *Attorney, Agent, or Firm*—Dean W. Russell; Kilpatrick Stockton LLP

(57) ABSTRACT

Individual respiratory gas supply device comprising a respiratory mask and a facial respirator of the cannula or respiratory flexible oro-nasal shell type for comfortably supplying a subject with respiratory gas during a high-altitude flight. The respiratory mask and the facial respirator are adapted so that in the event of de-pressurization or the presence of toxic gases, the subject equips himself with the respiratory mask possibly after having previously removed the facial respirator. Switching means make it possible to cut off the oxygen supply of the facial respirator and dispense oxygen to the regulator when the subject is equipped with the respiratory mask.

11 Claims, 3 Drawing Sheets

INDIVIDUAL RESPIRATORY GAS SUPPLY DEVICE INCLUDING A RESPIRATORY MASK AND A FACIAL RESPIRATOR

This application claims priority to French Patent Application No. 0210555 filed on Aug. 23, 2002, the entire contents of which are incorporated herein by reference.

The present invention relates to individual respiratory gas supply devices.

More particularly, the invention relates to an individual respiratory gas supply device comprising a respiratory mask for supplying a subject with respiratory gas, specially during a high-altitude flight, this mask itself comprising an oro-nasal facepiece suitable for covering the subject's mouth and nose, thereby providing a substantially leaktight junction with the subject's face, this facepiece being connected to an oxygen flow regulator, supplying the facepiece with respiratory gas from an oxygen dispenser.

Hereinbelow, the term "oxygen" will be used to denote either pure oxygen coming from a storage tank, or air which is highly enriched with oxygen.

The invention has a particularly important, although not exclusive, application in protecting pilots of civil aircraft who are likely to fly at high altitudes. International regulations require that at least one of the pilots continuously wears a respiratory gas supply device above flight level 410. Continuously wearing an oro-nasal mask applied against the face by the holding harness is unpleasant and may become painful.

Document EP-A-0691871 describes an example of such a device used in particular by the crew of transport aircraft.

This type of device must fulfil three functions:

1) protection against hypoxia in the event of accidental decompression at a high altitude of the aircraft cabin;
2) in-flight protection against a toxic environment in the event of fire or smoke; and
3) special protection against the risk of acute hypoxia due to the rapid nature of accidental decompression occurring at a flight altitude greater than 10668 metres (35,000 feet).

For the two first functions, the individual respiratory gas supply device must allow pure oxygen (or an equivalent gas) or a mixture enriched with oxygen to be inhaled. These first two functions are protective functions which correspond to a life-threatening emergency and both of which require a high degree of reliability in the quality of gas delivered to the subject. Consequently, the respiratory mask must be strictly leaktight.

For the third function, the individual respiratory gas supply device must allow preventive suroxygenation to be delivered to the pilot under normal flight conditions in order to avoid a loss of consciousness a few seconds after the decompression, even after applying a respiratory mask supplied with oxygen. This third function is a preventive function, above 10,668 metres (35,000 feet), which corresponds to normal flight conditions and normal aircraft pressurization conditions. It requires the mask to be continuously worn by the flight personnel. Now, this is a particularly uncomfortable preventive measure for the crews, especially when the respiratory mask is a protective mask with an optical screen, of the "full-face" type, which restricts the field of view.

The aim of the present invention is especially to alleviate this drawback.

As will be indicated more completely hereinbelow, the invention especially aims to provide the protection required for high-altitude flights by reducing the length of time during which an oro-nasal mask is worn, possibly with the addition of a protective visor for the eyes, to periods where such wearing is indispensable for protection against hypoxia and/or smoke.

To this end, provision is made, according to the invention, for an individual respiratory gas supply device which, apart from the characteristics already mentioned, is characterized by the fact that it comprises:

- a facial respirator adapted for delivering oxygen to at least one of the oro-nasal orifices of the subject by allowing inhalation of ambient air when the subject inspires, and
- means of switching the dispensing of oxygen between the respiratory mask and the facial respirator, adapted for cutting off the oxygen supply of the facial respirator and dispensing oxygen to the regulator from the dispenser when the subject wears the respiratory mask.

As already indicated, the first two functions mentioned above are protective functions. According to the invention, they are provided by the mask which can be hardened to comply with strict criteria for protection against hypoxia, especially in the area of leaktightness. This makes it barely comfortable, but these functions only have to be provided in very rare emergency situations. It is accepted that comfort in the mask is therefore not an essential criterion.

On the other hand, the last function is provided by the facial respirator. The latter may be worn in normal flight and allows the third function to be comfortably fulfilled. The third function, which is a preventive measure, does not necessarily require great accuracy in the administration of the oxygen-enriched gas mixture to the subject wearing it, the only constraint being that the inhaled gas mixture must contain at least a certain proportion of oxygen. The accuracy of the mixture, therefore the leaktightness of this equipment, is not critical. For this preventive oxygenation function in the cabin, the facial respirator complies as far as possible with the requirement of comfort. In the event of decompression or of the presence of toxic gases in the cabin, the subject wearing the facial respirator replaces this preventive equipment with a respiratory mask or superimposes this mask thereon.

In particular embodiments of the invention, one and/or another of the following arrangements are additionally available:

- the facial respirator comprises a nasal cannula;
- the facial respirator comprises a flexible oro-nasal shell;
- the respiratory mask is suitable for being worn when the subject is already wearing the facial respirator; or, on the other hand, it is the facial respirator which is adapted to be worn under a respiratory mask of conventional design; for example the facial respirator comprises supply branches which are flexible enough to be crushed between the face and the respiratory mask so as to conserve good sealing of the latter;
- the facial respirator is supplied with oxygen, from the oxygen dispenser;
- the switching means for dispensing oxygen are inserted both between the respiratory mask and the oxygen dispenser and between the facial respirator and the oxygen dispenser;
- the facial respirator and the oxygen dispenser are suitable for enriching the air inhaled by the subject by 40% oxygen, using the facial respirator;
- the facial respirator and the oxygen dispenser feed the subject using the facial respirator with a continuous flow;

the facial respirator and the oxygen dispenser supply the subject using the facial respirator with a pulsed flow solely during the inspiratory phase of the subject's respiratory cycle; and the facial respirator and the oxygen dispenser supply the subject using the facial respirator with a continuous flow rate, varying as a function of the actual inspiratory demand of the subject.

Other aspects, aims and advantages of the invention will become apparent on reading the description of some of its embodiments.

The invention will also be better understood with the help of the drawings, in which.

In the various figures, the same references denote identical or similar elements.

One embodiment of the individual respiratory gas supply device according to the invention is shown hereinbelow in a detailed manner.

Figure 1:
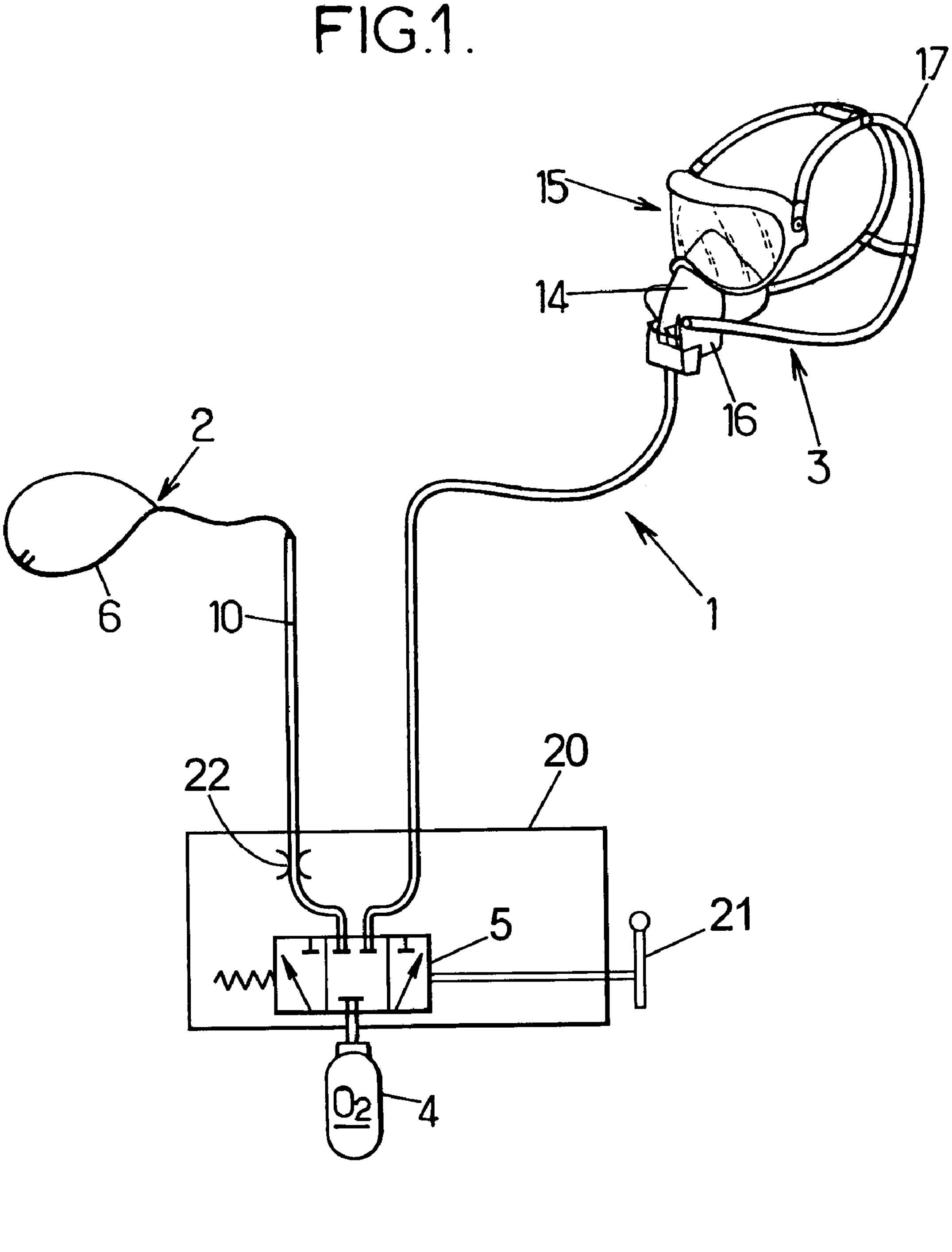
FIG. 1 shows schematically an example of an individual respiratory gas supply device according to the present invention.

According to this embodiment, as shown in FIG. 1, the individual respiratory gas supply device comprises a facial respirator 2, a respiratory mask 3, an oxygen dispenser 4 and switching means 5 for dispensing oxygen.

The oxygen dispenser 4 consists of an oxygen tank and/or an oxygen generating system, for example of the OBOGS type.

Figure 2:
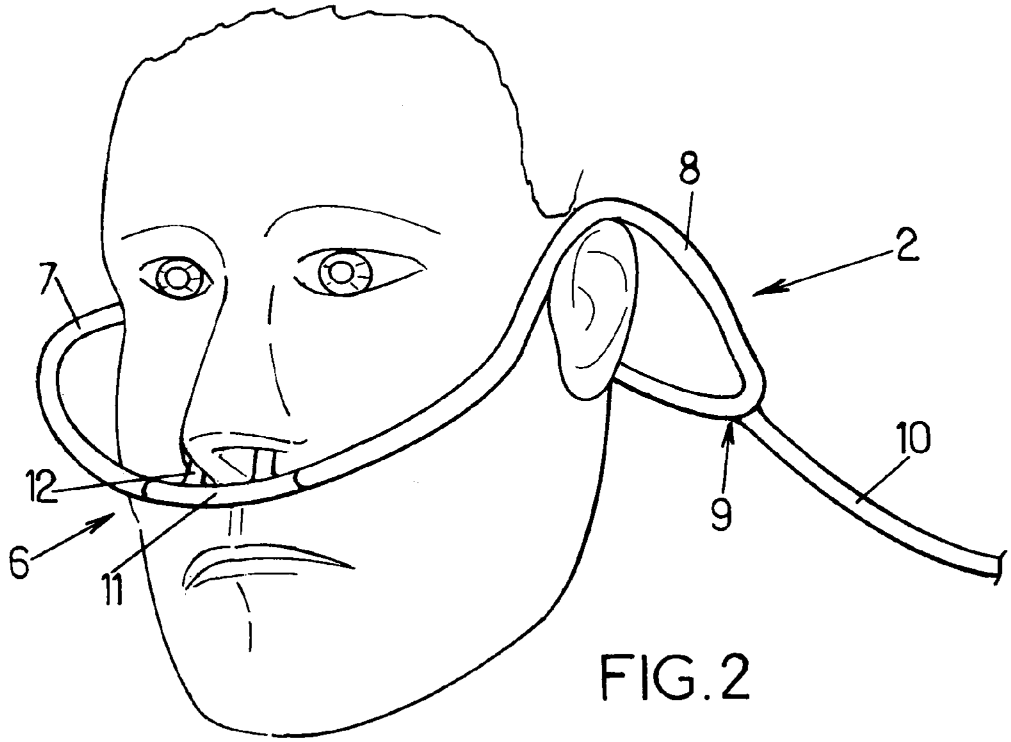
FIG. 2 shows schematically in perspective a facial respirator equipped with the individual supply device shown in FIG. 1.

As shown in FIGS. 1 and 2, the facial respirator 2 consists, for example, of a nasal cannula 6. This cannula comprises a pair of branches 7, 8. These branches 7, 8 are each suitable for being retained respectively over a subject's ear. These branches are connected together, on the one hand at a Y-shaped junction 9 opening out on to a supply pipe 10 for the two branches 7, 8, and on the other hand, at an inhalation sleeve 11. The common supply pipe 10 is connected to the oxygen dispenser 4 via the switching means 5 for dispensing oxygen. The inhaler sleeve opens out into two outlet pipes 12 each one designed to be placed in one nostril of the subject.

When a subject wears the cannula 6 the Y-shaped junction 9 is placed behind his head, substantially between his ears, the inhaler sleeve 11 is placed under his nose and each outlet pipe 12 is placed in one of his nostrils.

Figure 3:
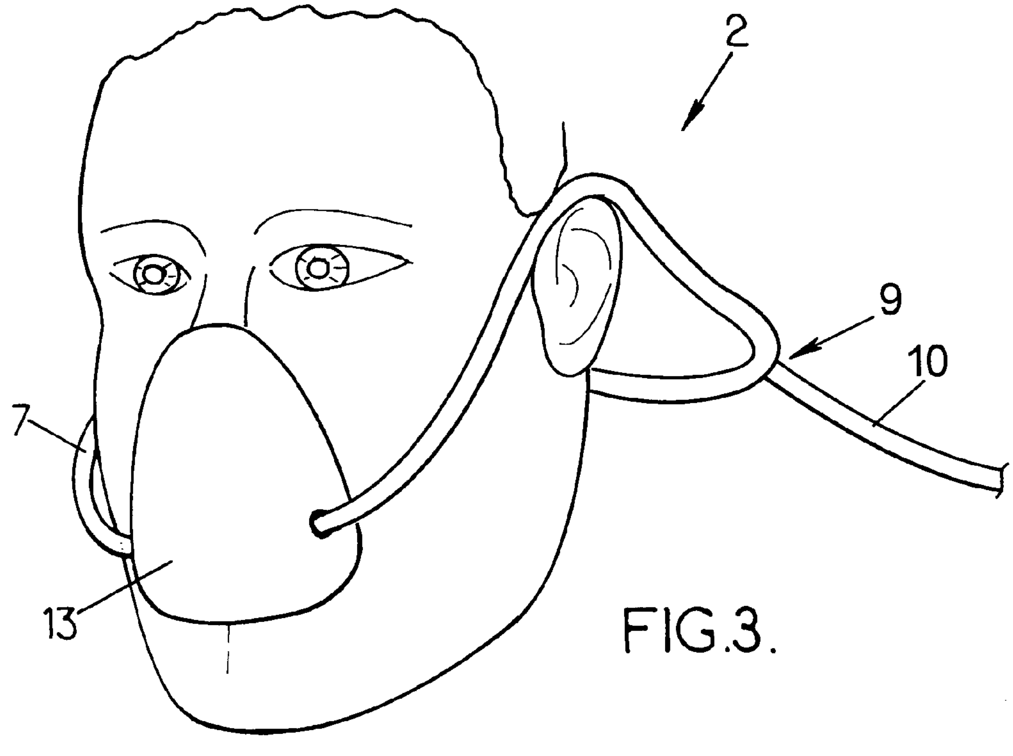
FIG. 3 shows schematically in perspective another example of a facial respirator constituting the individual supply device shown in FIG. 1.

According to a variant, illustrated in FIG. 3, the inhalation sleeve 11 is replaced by a flexible oro-nasal shell 13. This oro-nasal shell 13 does not cover the user's mouth and nose in a sealed manner so as to allow an intake of air which will be mixed with the oxygen taken in under this oro-nasal shell 13.

Optionally, the oro-nasal shell 13 is only a mask under which a cannula similar to the one described above is placed.

This oro-nasal shell 13 may be suitable for allowing correct and sufficient phonation for the effective use of a microphone like those conventionally worn by flight personnel of aircraft.

Many other variants of the facial respirator 2 may be envisaged. Some importance may in particular be attached to its aesthetic appearance. This is because there may be a benefit in that a pilot wearing the facial respirator 2 of the device 1 according to the invention does not appear to be a patient provided with medical respiratory assistance apparatus.

The cannula 6 and the oro-nasal shell 13 of the individual respiratory gas supply device 1 according to the invention advantageously allow the subject wearing them to communicate audibly without using a microphone.

The cannula 6 and the oro-nasal shell 13 of the individual respiratory gas supply device 1 according to the invention are inexpensive and may therefore be for single use, for hygiene purposes. In this case, the facial respirator 2 is advantageously stored in a sealed packaging and has an endpiece which can be directly plugged into the oxygen supply.

The respiratory mask 3 is, for example, a mask referred to as "full-face". Such a respiratory mask is, for example, described in document EP-A-069 187 1.

Figure 4:
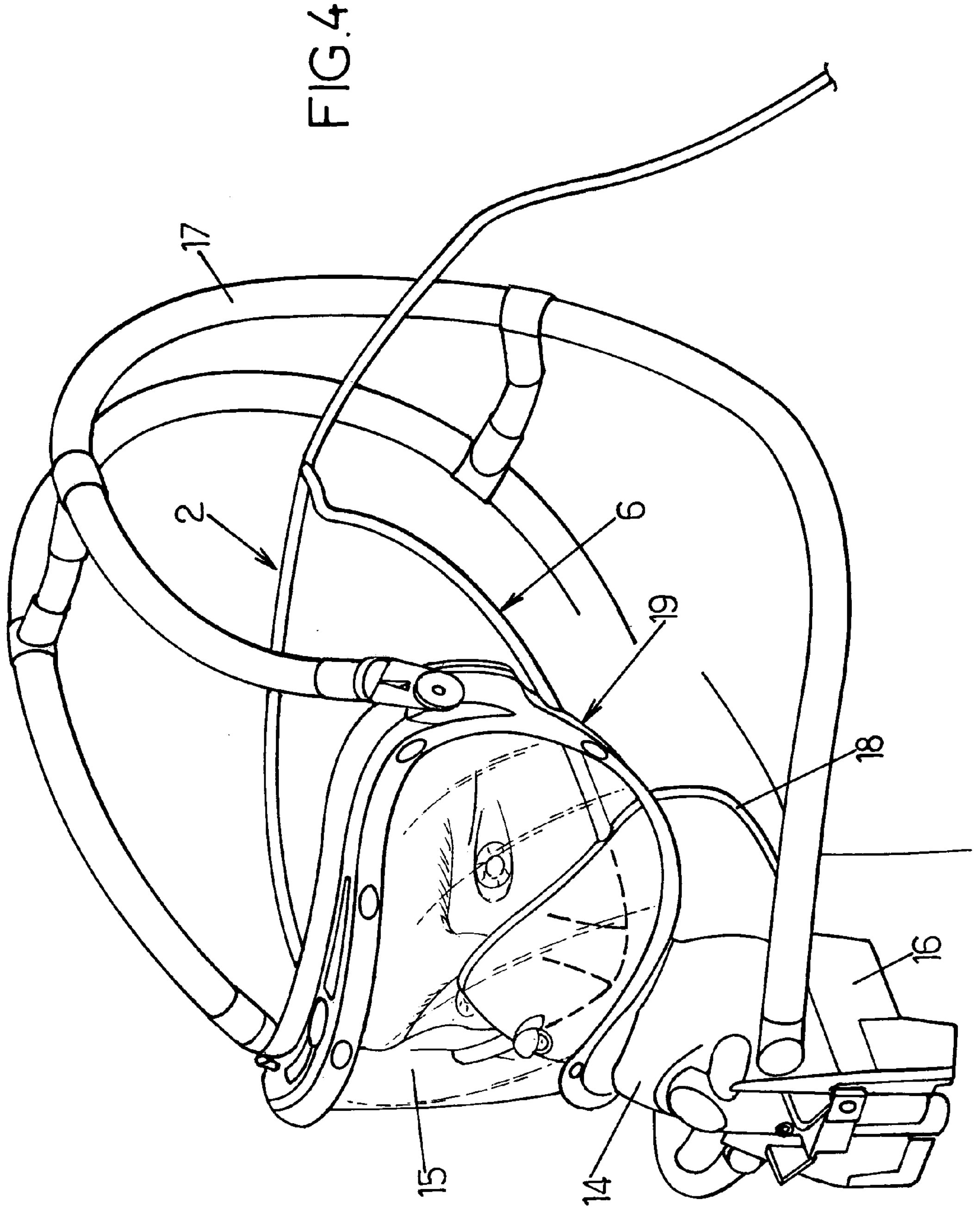
FIG. 4 shows schematically in perspective a subject wearing, above the facial respirator shown in FIG. 2, a respiratory mask of the individual respiratory gas supply device shown in FIG. 1.

As shown in FIGS. 1 and 4, this eye-protection mask 3 comprises an oro-nasal facepiece 14, a screen 15, a demand regulator 16 and a quick-placement harness 17. The regulator 16 and the harness 17 are of a generally known construction. The oro-nasal facepiece 14 is suitable for covering the mouth and the nose of the subject wearing it, thereby providing a substantially leaktight junction with the subject's face. Preferably, it comprises a seal 18 which may consist of an inner fold of the edge.

The screen comprises a transparent window having an optical quality, provided with a flexible frame, the edges of which are trapped in a seal 19.

The respiratory mask 3 is connected to the oxygen dispenser 4 via a mask box 20 and the switching means 5 for dispensing oxygen.

The seal 19 of the screen 15 and that 18 of the oro-nasal facepiece 14 are of the type generally designed for respiratory masks 3. The branches 7, 8 are flexible enough to allow a conventional respiratory mask 3 to be worn effectively, without damaging its leaktightness. The facial respirator is designed so that the respiratory mask 3 can be used without removing the facial respirator 2, while substantially preserving all the leaktight properties of the respiratory mask 3.

The switching means 5 for dispensing oxygen are fitted into the mask box 20.

The switching means 5 for dispensing oxygen comprise a valve 21. This valve 21 has three stable operating positions:

a closed position a first open position, in which only the cannula 6 is supplied with oxygen by the oxygen dispenser 4; and a second open position, in which only the respiratory mask 3 is supplied with oxygen by the oxygen dispenser 4.

Switching from the closed position to the first open position takes place by a manual operation of the user when he uses the facial respirator 2. According to a variant, switching from the closed position to the first open position takes place automatically when the facial respirator 2 is taken out of a storage housing or when the facial respirator is plugged in.

In the first open position, the facial respirator 2 is supplied through a calibrated orifice 22 located down-stream of the valve 21 and of the oxygen dispenser 4. This calibrated orifice 22, supplied at the pressure of the oxygen expanded by a pressure-reducing valve (not shown) downstream of the oxygen dispenser 4, guarantees a stable flow whatever the pressure at the outlet of the oxygen dispenser 4.

Switching from the closed position, or from the first open position, to the second open position takes place automatically when the respiratory mask 3 is taken out of the mask box 20.

Apart from abnormal flight conditions, the preventive supply of oxygen to flight personnel is provided by just the cannula 6. The switching means 5 for dispensing oxygen are in a position such that only the cannula 6 is supplied with oxygen.

In the preoxygenation situation under normal flight conditions, the oxygen dispenser 4 delivers oxygen with a continuous flow, or with a pulsed flow just during the inspiratory phase of the ventilation cycle, or else, with a continuous flow varying as a function of the actual inspiratory demand.

In the case of accidental de-pressurization, fire or the presence of toxic gases, the user takes hold of the respiratory mask 3 which is in the mask box 20. On opening this box 20, a signal is sent to the switching means 5 for dispensing oxygen. The switching means 5 for dispensing oxygen then cut the oxygen supply to the cannula 6 and directly supply the respiratory mask 3 with oxygen.

When the user wears, in the preoxygenation situation under normal flight conditions, the variant of the facial respirator 2 in the form of a shell 13, and when he is equipped with the respiratory mask 3 over this facial respirator 2, oxygen is dispensed by the respiratory mask 3. In this case, the switching means 5 for dispensing oxygen trigger an adjustment of the oxygen supply appropriate for this situation.

For example, according to this variant of the invention, in the preoxygenation situation, the oxygen is dispensed according to a simplified mode. The deployment of the respiratory mask 3 corresponding to an actual emergency causes switching to high-performance oxygen regulation, of conventional type. This switching may be at the same time as that of other services such as switching on a microphone.

According to a variant, the supply to the cannula 6 is only cut off by the switching means 5 for dispensing oxygen when the respiratory mask 3 is in place and is operational. In this case, controlling the switching means 5 for dispensing oxygen takes place manually by the subject himself, or else automatically after a time period of a few seconds or else by a physical interaction of the facial respirator 2 with the respiratory mask 3.

The facial respirator 2 may also be removed before the respiratory mask 3 is put in place.

What is claimed is:

1. An individual respiratory gas supply device comprising a respiratory mask for supplying a subject with respiratory gas, especially during a high-altitude flight, the mask itself comprising an oro-nasal facepiece adapted for covering the mouth and nose of the subject, thereby providing a substantially leaktight junction with the face of this subject, the facepiece being connected to an oxygen flow regulator supplying the facepiece with respiratory gas from an oxygen dispenser, comprising:

a facial respirator adapted for delivering oxygen to at least one of the oro-nasal orifices of the subject without preventing inhalation of ambient air when the subject inspires, and means of switching the dispensing of oxygen between the respiratory mask and the facial respirator, adapted for cutting off the oxygen supply of the facial respirator and dispensing oxygen to the regulator from the dispenser when the subject wears the respiratory mask.

2. The device according to claim 1 wherein the facial respirator comprises a nasal cannula.

3. The device according to claim 1 wherein the facial respirator comprises a flexible oro-nasal shell.

4. The device according to claim 1 wherein the respirator mask is adapted to be worn when the subject is already wearing the facial respirator.

5. The device according to claim 1 wherein the facial respirator is suitable for being worn under the respiratory mask.

6. The device according to claim 1 wherein the facial respirator is supplied with oxygen from the oxygen dispenser.

7. The device according the claim 6 wherein the switching means for dispensing oxygen are inserted both between the respiratory mask and the oxygen dispenser and between the facial respirator and the oxygen dispenser.

8. The device according to claim 1 wherein the facial respirator and the oxygen dispenser are suitable for enriching the air inhaled by the subject by 40% oxygen, using the facial respirator.

9. The device according to claim 8 wherein the facial respirator and the oxygen dispenser feed the subject using the facial respirator with a continuous flow.

10. The device according to claim 8 wherein the facial respirator and the oxygen dispenser supply the subject using the facial respirator with a continuous flow rate, pulsed only during an inspiratory phase of a respiratory cycle of the subject.

11. The device according to claim 8 wherein the facial respirator and the oxygen dispenser supply the subject using the facial respirator with a continuous flow rate, varying as a function of the actual inspiratory demand of the subject.

* * * * *